United States Patent [19]

Furey et al.

[11] Patent Number: 4,799,485

[45] Date of Patent: Jan. 24, 1989

[54] NEONATAL SUBGLOTTISCOPE SET

[75] Inventors: Andrew J. Furey, Philadelphia; Frederic P. Rosenwald, Churchville, both of Pa.

[73] Assignee: Pilling Co., Fort Washington, Pa.

[21] Appl. No.: 61,871

[22] Filed: Jun. 11, 1987

[51] Int. Cl.$^4$ ............................................. A61B 1/06
[52] U.S. Cl. ....................................... 128/11; 128/13
[58] Field of Search ....................... 128/10, 11, 12, 13, 128/7, 9

[56] References Cited

U.S. PATENT DOCUMENTS

| | | | |
|---|---|---|---|
| 3,592,199 | 7/1971 | Ostensen | 128/11 |
| 4,294,235 | 10/1981 | Storz | 128/11 |
| 4,406,280 | 9/1983 | Upsher | 128/11 |
| 4,557,256 | 12/1985 | Bauman | 128/11 |
| 4,567,882 | 2/1986 | Heller | 128/11 |

FOREIGN PATENT DOCUMENTS

| | | | |
|---|---|---|---|
| 375491 | 6/1932 | United Kingdom | 128/11 |
| 612116 | 11/1948 | United Kingdom | 128/11 |
| 806467 | 12/1958 | United Kingdom | 128/11 |

OTHER PUBLICATIONS

Mueller Catalog; *The Surgical Armamentarium;* 1980; pp. 779, 782, 783, 836, 1214, 1215.

Woodrow, Jack H., "Improved Suspension Laryngoscope for Use With Operative Microscope", Transactions American Academy of Ophthalmology and Otolarynology, Mar.-Apr. 1971, p. 412.

Pilling Catalog "Laryngo-Bronchoesophagology", 1975, pp. 12-26B.

Pilling Catalog of "Cardiovascular, Thoracic and General Surgical Instruments", 1979, p. 301.

Drawings of Pending Design patent application 062,045, filed by Applicants on Jun. 11, 1987.

*Primary Examiner*—Richard C. Pinkham
*Assistant Examiner*—Mark S. Graham
*Attorney, Agent, or Firm*—Howson & Howson

[57] ABSTRACT

A neonatal subglottiscope set for emergency use comprises a plurality of subglottiscope tubes of various sizes suitable for neonatal use and a handle. These tubes are detachably connectable to the handle by means of a lever-operated latch. Each tube has a passage along its wall for receiving a fiberoptic light carrier, which is bent 90 degrees near its proximal end, and which has a locating pin receivable in a hole located in an ear on the handle. The entrance opening of the light carrier-receiving passage on its subglottiscope tube is positioned on the wall of the tube so that when the tube is attached to the handle, the entrance opening in all cases is at a uniform predetermined distance from the hole in the ear on the handle which receives the locating pin of the light carrier. Consequently, the same light carrier and handle can be used with all of the tubes in the set. Removability of the subglottiscope tube from the handle allows the subglottiscope tube to be safely inserted in the larynx of the patient by eliminatng the possibility of exerting excessive leverage through the handle as the tube is inserted. The handle is a two-part handle having a first section directly attachable to the subglottiscope tube for manual movement of the tube after insertion, and the second section being attachable to the first section and usable to connect the subglottiscope tube to a laryngoscope support.

7 Claims, 2 Drawing Sheets

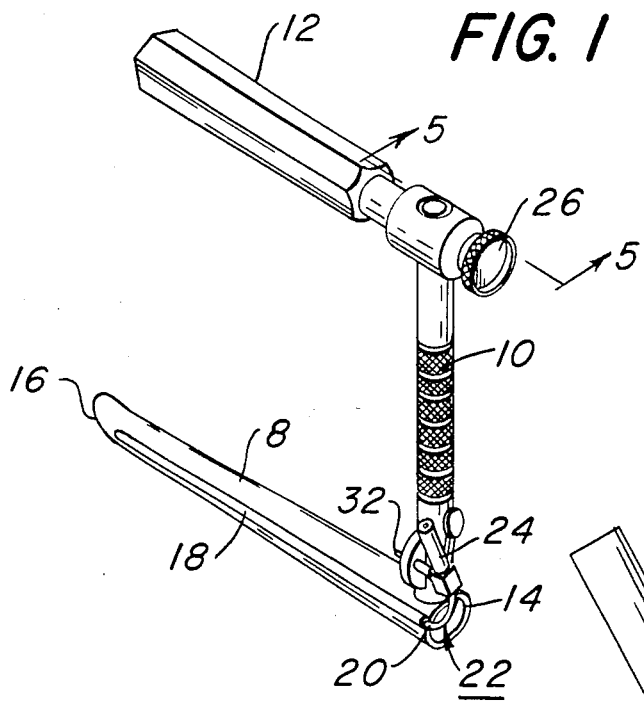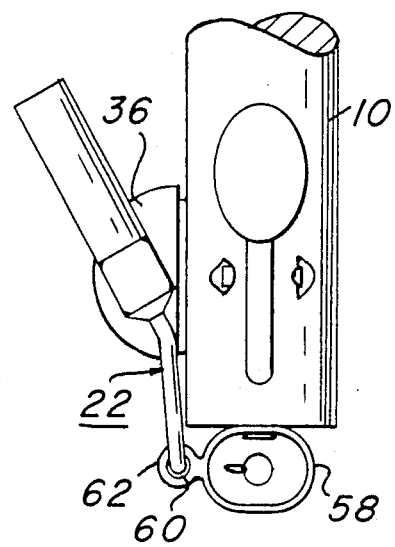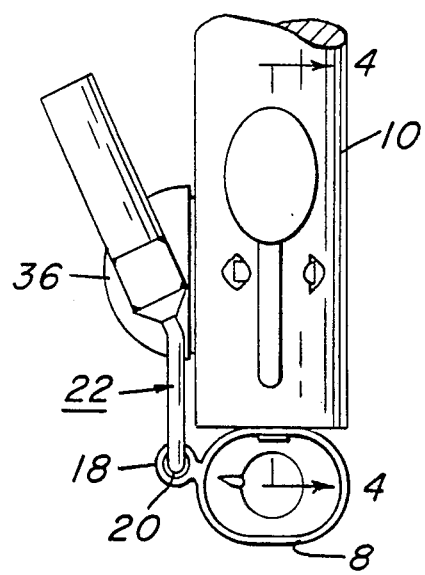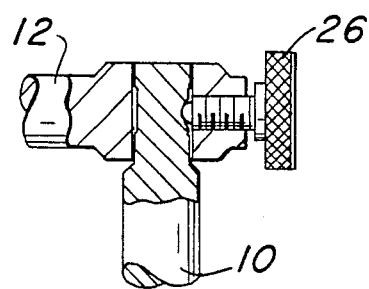

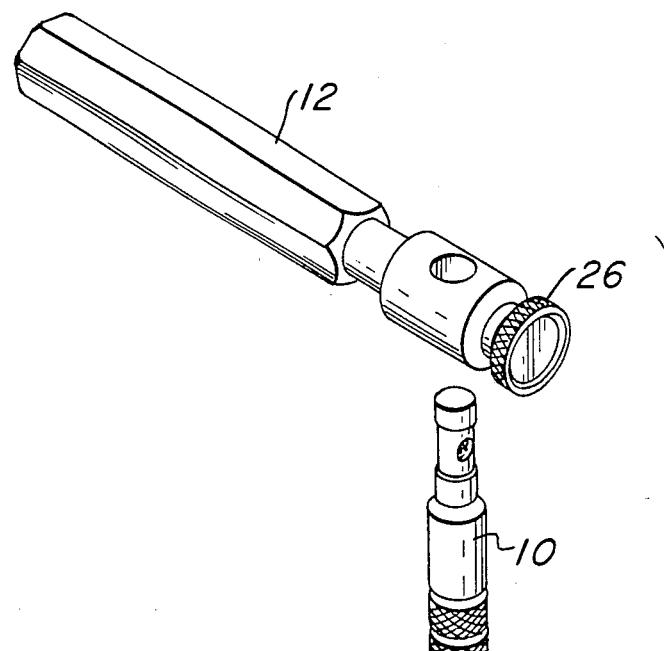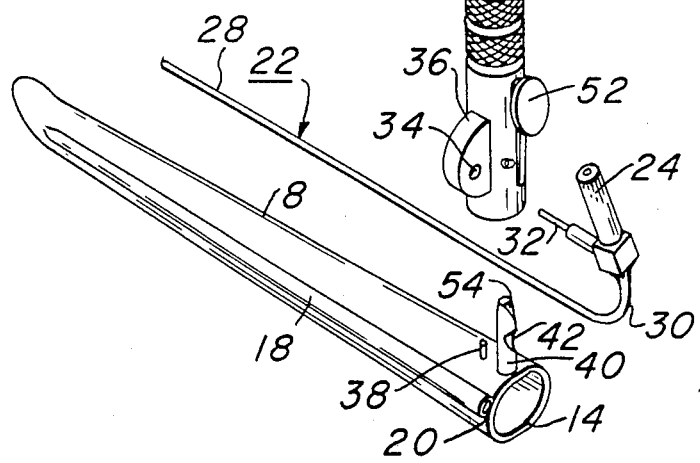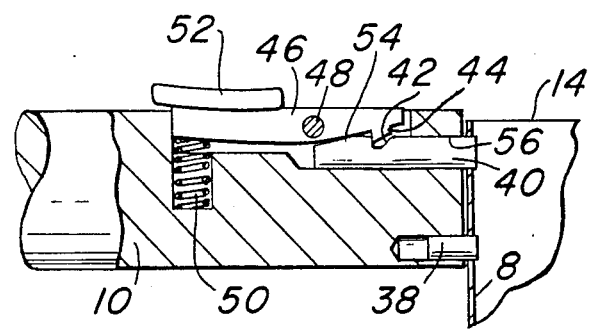

NEONATAL SUBGLOTTISCOPE SET

BRIEF SUMMARY OF THE INVENTION

This invention relates to laryngoscopy, and more specifically to a neonatal laryngoscope set. A neonatal laryngoscope (which can also be referred to as a neonatal subglottiscope) is intended to meet the medical needs of a premature or full term infant with upper respiratory or airway distress.

Most premature, and some full term infants experience upper respiratory or airway distress at birth or shortly thereafter. These conditions can be caused by stenosis of the trachea, stricture of the trachea, underdeveloped trachea and lungs, or excessive mucus in the upper respiratory area. Whenever any of these conditions is encountered, the airway must be opened and cleared immediately. No satisfactory instrument has heretofore been made available to meet these problems. In the past, upper respiratory and airway distress were relieved either by the use of a suction tube, or by an immediate tracheotomy.

The subglottiscope set in accordance with the invention is designed to allow the physician to clear the infant's airway immediately. It also useful in the diagnosis of upper respiratory distress, and in connection with laser treatment of tracheal and subglottic stenoses.

The principal object of this invention is to provide an instrument set which is usable on infants through a full range of sizes from premature to full term, which can be used rapidly and effectively to relieve airway distress when needed, and which reduces the likelihood of injury to the patient.

The subglottiscope set in accordance with the invention comprises a plurality of elongated hollow tubes of different sizes, each being adapted to enter the larynx of a newborn patient, and each having a tubular wall with a central axis and having proximal and distal ends. Each tube has a passage means extending along its wall for removably receiving a fiberoptic light carrier. The passage has an entrance opening adjacent to the proximal end of the tube. The set also includes a handle, to which any of the tubes of the set can be removably and rigidly attached. It also includes a rigid fiberoptic light carrier having a first portion adapted to enter the passage of each of the tubes. The light carrier has coupling means for attachment to a light source through a flexible light guide, and a curved portion connecting the first portion to the coupling means so that the flexible light guide does not obstruct the physician's line of vision through the tube.

Each of the tubes is approximately 12 centimeters in length, with its opening at the distal end being approximately circular and with an oval-shaped opening at the proximal end. Each tube has an internal diameter at its distal end less than approximately 8 millimeters. The maximum internal dimension at the proximal end is between approximately 9.9 and 11.1 millimeters, and the minimum internal dimension at the proximal end is between approximately 7.5 and 9.9 millimeters. Preferably four tubes are provided having internal diameters at their distal ends of approximately 3, 4, 5 and 6 millimeters respectively.

The coupling means of the light carrier has a pin projecting in a direction parallel to the first portion of the light carrier, and the handle has a hole for receiving the pin. Engagement of this pin and hole prevent the light carrier from being rotated. This reduces the likelihood of accidental removal of the light carrier from the light carrier receiving passage by forces imparted by the light-conducting cable to which the light carrier is connected. Although the distance between the entrance of the light carrier receiving passage and the central axis of the tube differs from tube to tube, the light carrier receiving passage is positioned on each tube so that when the tube is connected to the handle, the distance between the pin receiving hole of the handle and the entrance opening at the proximal end of the light carrier receiving tube is the same regardless of which tube is attached to the handle. This way, a single light carrier can be used with all of the tubes.

Among the advantages of the invention are the fact that each tube is detachable from the handle, allowing the physician to insert the tube by itself. This reduces the occurrence of injury to the infant because the leverage of the handle is eliminated. A first section of the handle can be readily attached to the tube, after the tube is inserted into the patient's trachea, in order to facilitate manipulation of the tube. The handle is a two-part handle, having a second section which can be attached to the first section, enabling the instrument to be secured to a conventional laryngoscope support.

Another advantage of the invention is the fact that the removability of the tubes from the handle allows a single handle assembly to serve multiple tubes. The fact that several tubes are served by a single handle assembly and by a single light carrier, significantly reduces the cost of the subglottiscope set.

Another important advantage resulting from the use of a single light carrier serving multiple subglottiscope tubes is the fact that in an emergency situation, no time need be wasted in searching among several different sizes of light carriers for the carrier corresponding to a particular subglottiscope tube.

Additional objects and advantages of the invention will be apparent from the following detailed description when read in conjunction with the drawings.

BRIEF DESCRIPTION OF THE DRAWINGS

FIG. 1 is a perspective view of a neonatal subglottiscope assembly in accordance with the invention;

FIG. 2 is an exploded view of the subglottiscope assembly;

FIG. 3 is a fragmentary elevational view from the proximal end of the tube of a subglottiscope assembly comprising a first tube connected to the handle;

FIG. 4 is a vertical section taken on plane 4—4 of FIG. 3, showing the latch by which the tube is attached to the handle;

FIG. 5 is a vertical section taken on plane 5—5 of FIG. 1, showing how the two parts of the handle are attached together; and FIG. 6 is a fragmentary elevational view corresponding to FIG. 3, but showing a smaller subglottiscope tube attached to the same handle.

DETAILED DESCRIPTION

The invention is a subglottiscope set comprising a handle, a light carrier, and a plurality of subglottiscope tubes any one of which can be used with the handle and light carrier to provide a complete subglottiscope.

A subglottiscope in accordance with the invention and as shown in FIG. 1, has three parts, a subglottiscope tube 8, and a handle comprising a first section 10, and a second section 12. The first section of the handle extends substantially perpendicular to the tube from a point near the proximal end 14 of the tube. The second section 12 of the handle is connected to the opposite end of section 10, and extends in the direction of, and parallel to tube 8.

Tube 8 is tapered, the proximal end 14 being somewhat larger in size than the distal end 16. The tube is approximately 12 centimeters in length. The opening of the distal end is substantially circular, and has an internal diameter of less than approximately 8 millimeters. The opening at the proximal end 14 is oval in shape, and has a maximum internal dimension between approximately 9.9 and 11.1 millimeters, and a minimum internal dimension between approximately 7.5 and 9.9 millimeters.

A passage 18 is formed along the wall of tube 16, and extends from an entrance opening 20 adjacent to proximal end 14 of the tube, to an exit opening (not shown in FIG. 1) adjacent to distal end 16 of the tube. The entrance opening is located immediately adjacent to the outer wall of tube 16, and passage 18 extends through the wall so that its exit opening is located immediately adjacent to the inner wall of tube 16. Passage 18 receives a substantially rigid metal-clad fiberoptic light carrier 22, which has a coupling 24 adapted to be removably connected to a flexible light conductor. As shown in FIG. 1, coupling 24 extends approximately perpendicular to the direction of elongation of passage 18. Consequently, the flexible light conductor connected to coupling 24 does not interfere with the physician's attempt to look through tube 8. Handle section 12 is clamped onto handle section 10 by means of a clamping screw 26, also shown in FIG. 5. Handle section 12 has a hexagonal cross-section, adapted to be received in the clamp of a first type of subglottiscope support. The end of handle section 12 remote from screw 26 has a threaded opening (not shown), which is adapted to receive the attachment screw of an alternative type of subglottiscope support known as a "Boston suspension".

As shown in FIG. 2, light carrier 22 has a straight portion 28 adapted to enter opening 20 of passage 18 and to extend through passage 18 to a location near the distal end of tube 8. Light carrier 22 has a curved section 30 which connects straight section 28 with coupling 24. A locating pin 32 extends from coupling 24 in a direction parallel to straight section 28 of the light carrier. This pin is adapted to enter hole 34 in ear 36 of handle section 10. The cross-sections of straight portion 28 of the light carrier are circular as is the interior wall of passage 20. The engagement of pin 32 in hole 34, however, prevents the light carrier from rotating in passage 18 as a result of forces applied to coupling 24 by the light-conducting cable to which coupling 24 is connected. The engagement of pin 32 in hole 34 greatly reduces the tendency of the light carrier to move.

As shown in FIGS. 2 and 4, tube 8 has a locating pin 38 extending perpendicularly outwardly from its wall near the proximal end 14 of the tube. Adjacent to pin 38 is a latching pin 40, which also extends outwardly perpendicularly from wall 14. Latching pin 40 has a notch 42, which, as shown in FIG. 4, cooperates with a detent 44 of lever 46, which is pivoted on pin 48 and urged by compressed coil spring 50 so that detent 44 enters notch 42. On the side of pivot pin 48 remote from detent 44, lever 46 has a button 52 which, when depressed, causes detent 44 to disengage notch 42, allowing tube 8 to be detached from handle section 10. Pin 40 is tapered at 54 so that, when pin 40 is inserted into hole 56 in the end of handle section 10, lever 46 is rotated so that detent 44 rides over surface 54 and drops into notch 42 whereby the tube and handle are automatically locked together. The tube and handle therefore snap together, and can easily be separated from each other by depressing pushbutton 52 and pulling them apart.

When the tube and handle are attached, the light carrier can be inserted into passage 18. When the light carrier is almost fully inserted, pin 32 enters hole 34 on handle 10.

Referring now to FIG. 3, tube 8 is attached to handle section 10, and light carrier 22 is inserted into passage 18, and has its pin 32 (not shown in FIG. 3) inserted into the hole in ear 36 of the handle. The position of the entrance opening 20 of passage 18 on the wall of tube 8 is such that the distance between entrance opening 20 and the hole in ear 36 is equal to the distance between the straight portion 28 and pin 32 of the light carrier. The same relationship holds true in FIG. 6, in which a smaller laryngoscope tube 58 is connected to handle section 10. Entrance opening 60 of its light carrier passage 62 is positioned on the wall of tube 58 so that when tube 58 is connected to handle section 10, the distance between entrance opening 60 and the hole in ear 36 is equal to the distance between the straight portion and pin 32 of the light carrier. As will be apparent by comparing FIGS. 3 and 6, the axis of the light carrier passage is the same distance from the wall of the subglottiscope tube in each case. However, the light carrier is rotated slightly counterclockwise in FIG. 6 as compared with its position in FIG. 3 because of the fact that the distance between entrance opening 60 and the central axis of tube 58 is slightly less than the distance between entrance opening 20 and the central axis of tube 8. The entrance openings of the light guide passages are positioned on the peripheries of the walls of the tubes so that in each case, when the tube is attached to handle section 10, the distance between the entrance opening of its light carrier passage and the axis of the hole in ear 36 is the same. Thus, the same light guide can be used with all of the tubes in the set.

The subglottiscope set of the invention is ideally suited for emergency treatment of newborns experiencing airway distress because it permits the physician to select a tube in the appropriate size, to insert it without the handle, thereby eliminating the possibility of exerting excess leverage through the handle during insertion and consequently reducing the likelihood of injury. Thereafter the physician may attach a first handle section for manipulation and a second separate handle section if a laryngoscope support is to be used. The positioning of the light carrier passage entrances on the tubes makes it possible to use the same light carrier with all of the tubes in the set. It is unnecessary, in an emergency, to search among several light carriers of similar appearance to find the one corresponding to the particular subglottiscope tube selected for use.

The laryngoscope set is, of course also well-suited for non-emergency diagnostic and surgical use.

The subglottiscope set can be modified in numerous respects, for example in the number of tubes provided, in the specific configuration of the handle and light carrier, and in many other respects, without departing from the scope of the invention as defined in the following claims.

1. A neonatal subglottiscope set for emergency use comprising:

a plurality of elongated hollow tubes of different sizes, each being adapted to enter the larynx of a patient, each having a tubular wall, a central axis, a proximal end and a distal end, and each tube having light carrier passage means extending along its wall for removably receiving a fiberoptic light carrier, said light carrier passage means having an entrance opening adjacent to the proximal end of the tube, in which the radial distance from the entrance opening of the light carrier passage means of each tube to the central axis of the tube is different for each of the tubes;

a handle;

means for rigidly and removably attaching each of the tubes to the handle; and a substantially rigid fiberoptic light carrier having a first portion adapted to enter the light carrier passage means of each of the tubes, coupling means for attachment of a light source to the light carrier, and a curved portion connecting the first portion to the coupling means;

said coupling means having a pin projecting therefrom in a direction parallel to the axis of the first portion, said handle having a hole for receiving said pin, and the light carrier passage means extending along the wall of each of the tubes having its entrance opening at a position on the wall of the tube such that, when any one of said tubes is connected to the handle by the attaching means, the entrance opening is at a predetermined distance from the hole of the handle and said pin and said entrance opening of said light carrier passage means being spaced at said predetermined distance such that the pin of the light carrier can enter the hole as the light carrier moves into the light carrier passage means.

2. A subglottiscope set according to claim 1 in which the first portion of the fiberoptic light carrier is straight and rotatable in the light carrier passage means.

3. A subglottiscope set according to claim 1 in which the exterior of the first portion of the fiberoptic light carrier has circular transverse cross-sections.

4. A subglottiscope set according to claim 1 in which each tube has a locking pin and a locating pin extending outwardly from the wall of the tube near the proximal end of the tube, and in which the handle has a first hole in one of its ends for receiving the locating pin, a second hole in the same end for receiving the locking pin, latch means for securing the locking pin in the second hole, and manually operable means for releasing the latch means to permit detachment of the handle from the tube.

5. A subglottiscope set according to claim 1 in which the handle comprises a first elongated section, a second elongated section, and means for detachably fastening said first and second elongated sections rigidly together with their directions of elongation substantially perpendicular to each other, said means for rigidly and removably attaching each of the tubes to the handle being adapted to connect each tube to the first section of the handle with the central axis of the tube substantially perpendicular to the direction of elongation of said first section and with the second section extending from the first section in the same direction in which the tube extends from the first section.

6. A subglottiscope set according to claim 1 in which the plurality of elongated hollow tubes includes four tubes having internal diameters at their distal ends of approximately 3, 4, 5 and 6 millimeters respectively.

7. A subglottiscope set according to claim 1 in which each of the tubes of the plurality of tubes is approximately 12 centimeters in length, has an internal diameter at its distal end less than approximately 8 millimeters, and a maximum internal dimension at its proximal end between approximately 9.9 and 11.1 millimeters, and a minimum internal dimension at its proximal end between approximately 7.5 and 9.9 millimeters.

* * * * *